US008329140B2

(12) United States Patent
Thorn et al.

(10) Patent No.: US 8,329,140 B2
(45) Date of Patent: Dec. 11, 2012

(54) METHOD AND SYSTEM FOR HYDROGEN EVOLUTION AND STORAGE

(75) Inventors: David L. Thorn, Los Alamos, NM (US); William Tumas, Los Alamos, NM (US); P. Jeffrey Hay, Los Alamos, NM (US); Daniel E. Schwarz, Los Alamos, NM (US); Thomas M. Cameron, Los Alamos, NM (US)

(73) Assignee: Los Alamos National Security, LLC, Los Alamos, NM (US)

(*) Notice: Subject to any disclaimer, the term of this patent is extended or adjusted under 35 U.S.C. 154(b) by 1126 days.

(21) Appl. No.: 12/283,462

(22) Filed: Sep. 11, 2008

(65) Prior Publication Data

US 2011/0129411 A1   Jun. 2, 2011

Related U.S. Application Data

(62) Division of application No. 11/152,525, filed on Jun. 10, 2005, now Pat. No. 7,439,369.

(60) Provisional application No. 60/581,914, filed on Jun. 22, 2004, provisional application No. 60/616,085, filed on Oct. 5, 2004.

(51) Int. Cl.
*C01B 3/02* (2006.01)

(52) U.S. Cl. .......... 423/648.1; 423/644; 548/301.7; 548/302.7

(58) Field of Classification Search ............ 423/644, 423/648.1; 508/301.7, 302.7
See application file for complete search history.

(56) References Cited

U.S. PATENT DOCUMENTS

| | | | |
|---|---|---|---|
| 4,134,491 A | 1/1979 | Turillon et al. | |
| 5,527,979 A | 6/1996 | Agaskar et al. | |
| 5,817,891 A * | 10/1998 | Brocker et al. | 568/799 |
| 6,699,457 B2 | 3/2004 | Cortright et al. | |
| 2002/0103401 A1* | 8/2002 | Schelhaas et al. | 564/415 |
| 2003/0009943 A1 | 1/2003 | Millet et al. | |
| 2003/0099593 A1 | 5/2003 | Cortright et al. | |
| 2003/0170171 A1 | 9/2003 | Cortright et al. | |
| 2004/0022723 A1 | 2/2004 | Cortright et al. | |

OTHER PUBLICATIONS

Audrey Moores et al. "Catalysed low temperature H2 release from nitrogen heterocycles." New J. Chem., 2006, 30, pp. 1675-1678.*
Meijer et al., "Triruthenium Dodecacarbonyl/Triphenylphosphine Catalyzed Dehydrogenation of Primary and Secondary Alcohols," Tetrahedron, vol. 60, pp. 1065-1072, Jan. 2004.
Ligthart et al., "Highly Sustainable Catalytic Dehydrogenation of Alcohols with Evolution of Hydrogen Gas," Tetrahedron Letters, vol. 44, pp. 1507-1509, Feb. 2003.
Hodoshima et al., "Catalytic Decalin Dehydrogenation/Naphthalene Hydrogenation Pair as a Hydrogen Source for Fuel Cell Vehicle," International Journal of Hydrogen Energy, vol. 28, pp. 1255-1262, Nov. 2003.
Xu et al., "Thermochemical Alkane Dehydrogenation Catalyzed in Solution Without the Use of a Hydrogen Acceptor," Chemical Communications, pp. 2273-2294, Dec. 1997.
Brunet et al., "Formal Transfers of Hydride from Carbon-Hydrogen Bonds. Generation of $H_2$ from Orthoformamides Designed to Undergo Intramolecular Protonolysis of Activated Carbon-Hydrogen Bonds," Journal of Organic Chemistry, vol. 61, pp. 2020-2026, Mar. 1996.
Brunet et al., "Formal Transfers of Hydride from Carbon-Hydrogen Bonds. Attempted Generation of $H_2$ by Intramolecular Protonolysis of the Activated Carbon-Hydrogen Bonds of Dihydrobenzimidazoles," Canadian Journal of Chemistry, vol. 74, pp. 689-696, May 1996.
Hill et al., "The Conversion of Polysaccharides to Hydrogen Gas. Part III: The Conversion of Cellulose to Formic Acid/Formate Ion and Hydrogen," J. Chem. Tech. Biotechnol, 1988, vol. 41, pp. 173-181.
Hill et al., "The Conversion of Polysaccharides to Hydrogen Gas. Part II: The Catalytic Decomposition of Formaldehyde in the Aqueous Phase," J. Chem. Tech. Biotechnol, 1988, vol. 41, pp. 135-144.
Hill et al., "The Conversion of Polysaccharides to Hydrogen Gas. Part I: The Palladium Catalysed Decomposition of Formic Acid/Sodium Formate Solutions," J. Chem. Tech. Biotechnol, 1988, vol. 41, pp. 121-133.
Jung et al., "Dehydrogenation of Alcohols and Hydrogenation of Aldehydes Using Homogeneous Ruthenium Catalysts," Organometallics, 1982, vol. 1, pp. 658-666.
Williams et al., "Use of Carbon Dioxide in Energy Storage," Appl. Phys. Lett., vol. 33, pp. 1173-1174, Sep. 1978.

* cited by examiner

*Primary Examiner* — Paul Wartalowicz
(74) *Attorney, Agent, or Firm* — Samuel L. Borkowsky

(57) ABSTRACT

A method and system for storing and evolving hydrogen ($H_2$) employ chemical compounds that can be hydrogenated to store hydrogen and dehydrogenated to evolve hydrogen. A catalyst lowers the energy required for storing and evolving hydrogen. The method and system can provide hydrogen for devices that consume hydrogen as fuel.

5 Claims, No Drawings

METHOD AND SYSTEM FOR HYDROGEN EVOLUTION AND STORAGE

RELATED APPLICATIONS

This application is a divisional of U.S. application Ser. No. 11/152,525 filed Jun. 10, 2005 now U.S. Pat. No. 7,439,369, now allowed, and claims the benefit of U.S. Provisional Patent Application Ser. No. 60/581,914 filed Jun. 22, 2004, and U.S. Provisional Patent Application Ser. No. 60/616,085 filed Oct. 5, 2004, all hereby incorporated by reference.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to hydrogen evolution and storage and more particularly to a method and system for storing and evolving hydrogen.

BACKGROUND OF THE INVENTION

Hydrogen ($H_2$) is currently the leading candidate for a fuel to replace gasoline/diesel fuel in powering the nation's transportation fleet. There are a number of difficulties and technological barriers associated with hydrogen that must be solved in order to realize this "hydrogen economy". Inadequate storage systems for on-board transportation hydrogen are recognized as a major technological barrier (see, for example, "The Hydrogen Economy: Opportunities, Costs, Barriers, and R&D Needs," National Academy of Engineering (NAE), Board on Energy and Environmental Systems, National Academy Press (2004).

One of the general schemes for storing hydrogen relates to using a chemical compound or system that undergoes a chemical reaction to evolve hydrogen as a reaction product. In principle, this chemical storage system is attractive, but all practical systems that have been studied to date involve either: (a) hydrolysis of high-energy inorganic compounds where the evolution of hydrogen is very exothermic (sodium borohydride/water as in the Millennium Cell's HYDROGEN ON DEMAND®, and lithium hydride as in SAFE HYDROGEN®, for example), thus making the cost of preparing the inorganic compound(s) high and life-cycle efficiency low; or (b) dehydrogenation of inorganic hydride materials (such as $Na_3AlH_6/NaAlH_4$, for example) that release hydrogen when warmed but that typically have inadequate mass storage capacity and inadequate refueling rates.

Inorganic compounds referred to in (a), above, produce hydrogen according to the chemical reaction

where $MH_x$ is a metal hydride, and $M(OH)_x$ is a metal hydroxide. This reaction is irreversible.

Inorganic hydride materials referred to in (b), above, produce hydrogen according to following chemical reaction, which is reversible with $H_2$ (hydrogen gas):

where $MH_x$ is a metal hydride, M is metal and $H_2$ is hydrogen gas. By contrast to the first reaction, which is irreversible with $H_2$, the second reaction is reversible with $H_2$.

A practical chemical system that evolves hydrogen yet does not suffer the aforementioned inadequacies would be important to the planned transportation sector of the hydrogen economy. This same practical chemical system would also be extremely valuable for non-transportation $H_2$ fuel cell systems, such as those employed in laptop computers and other portable electronic devices, and in small mechanical devices such as lawnmowers where current technology causes significant pollution concerns.

Any heat that must be input to evolve the hydrogen represents an energy loss at the point of use, and any heat that is evolved along with the hydrogen represents an energy loss where the chemical storage medium is regenerated. Either way, energy is lost, which diminishes the life-cycle efficiency. For most organic compounds, such as in those shown in equations 3-5 below, hydrogen evolution reactions are very endothermic, and the compounds are incompetent to evolve hydrogen at ambient temperature (i.e. thermodynamically incapable of evolving $H_2$ at significant pressure at ambient temperature). For temperatures less than about 250-400 degrees Celsius, the equilibrium pressure of hydrogen over most organic compounds is very small. As a consequence, most common organic compounds require heating above about 250 degrees Celsius, and the continual input of high-grade heat to maintain this temperature, in order to evolve hydrogen at a useful pressure.

$$CH_4 \rightarrow C + 2H_2 \quad \Delta H^0 = +18 \text{ kcal/mol}$$

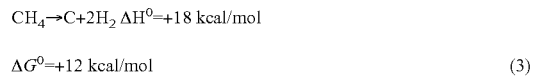

$$6CH_4 \rightarrow \text{cyclohexane} + 6H_2 \quad \Delta H^0 = +69 \text{ kcal/mol}$$

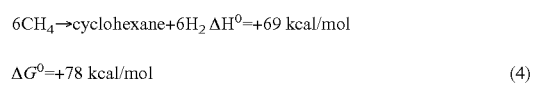

$$\text{cyclohexane} \rightarrow \text{benzene} + 3H_2 \quad \Delta H^0 = +49 \text{ kcal/mol}$$

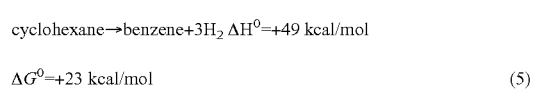

Most organic compounds have hydrogen evolution reactions that are endergonic (i.e. having a net positive free energy of reaction change, i.e. $\Delta G > 0$) and their ambient temperature equilibrium hydrogen pressure is very low, practically unobservable. Thus, most organic compounds are unsuitable for hydrogen storage, based on both life-cycle energy efficiency and delivery pressure considerations. Decalin, for example, evolves hydrogen to form naphthalene when heated to about 250 degrees Celsius in the presence of a catalyst (see, for example, "Catalytic Decalin Dehydrogenation/Naphthalene Hydrogenation Pair as a Hydrogen Source for Fuel-Cell Vehicle," S. Hodoshima, H. Arai, S. Takaiwa, and Y. Saito, Int. J. Hydrogen Energy (2003) vol. 28, pp. 1255-1262, incorporated by reference herein). Hodoshima et al. use a superheated "thin film" reactor that operates at a temperature of at least 280 degrees Celsius to produce hydrogen from decalin at an adequate rate. Thus, this endothermic hydrogen evolution reaction requires both a complex apparatus and high-grade heat, which diminishes the life-cycle energy efficiency for hydrogen storage.

Methods and systems that employ chemical compounds for storing and evolving hydrogen at ambient temperature with minimal heat input remain highly desirable.

Therefore, an object of the present invention is a method for evolving hydrogen that is thermodynamically more favored than previously-described systems.

Another object of the present invention is a thermodynamically favorable system for evolving hydrogen.

Another object of the present invention is a reversible system for evolving and storing hydrogen.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes a method for producing hydrogen ($H_2$). The method involves exposing at least one chemical compound to a catalyst under conditions suitable for dehydrogenating the at least one chemical compound to form at least one product, the at least one chemical compound having the formula

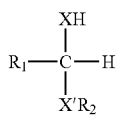

wherein X is oxygen, —N(H)—, or —N($R_3$)—; wherein X' is oxygen, —N(H)— or —N($R_4$)—; wherein $R_1$, $R_2$, $R_3$, and $R_4$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl sulfonic acid, alkenyl phosphoric acid, and alkenyl phosphonic acid; and wherein $R_1$ and $R_3$ can be connected to each other to form a ring structure; and with the proviso that X and X' cannot both be oxygen.

The invention also includes a method for producing hydrogen ($H_2$), and involves exposing at least one chemical compound to a catalyst under conditions suitable for chemical reaction that forms hydrogen. The chemical compound has the formula

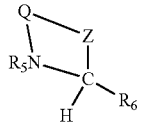

wherein Q is —(C($R_7R_8$))$_n$— where n is from 1 to 10, —(C($R_7R_8$)-M-C($R_7R_8$))—, —(C($R_7$)=C($R_8$))—, —(C($R_7$)=C($R_8$)—C($R_9$)=C($R_{10}$))—, —(C($R_7$)=N)—, or —(C($R_7$)=N—C($R_8$)=N)—; wherein M is oxygen, —N$R_9$—, sulfur, or —C(=O)—; wherein Z is oxygen, sulfur, or —N($R_{11}$)—; wherein $R_5$ and $R_{11}$ are independently selected from hydrogen, alkyl, and aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, and alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —O$R_{12}$, —N(H)($R_{12}$) and —N($R_{12}R_{13}$) wherein $R_{12}$ and $R_{13}$ are independently selected from hydrogen, alkyl and aryl; wherein $R_7$ and $R_8$ may be connected to each other to form a ring structure; wherein $R_8$ and $R_9$ may be connected to each other to form a ring structure; and with the proviso that at least one of $R_5$ or $R_{11}$ is hydrogen.

The invention also includes a method for producing hydrogen ($H_2$), comprising exposing at least one chemical compound and an acid to a catalyst under conditions suitable for chemical reaction that forms hydrogen. The chemical compound has the formula

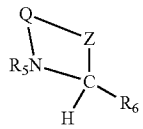

wherein Q is —(C($R_7R_8$))$_n$— where n is from 1 to 10, —(C($R_7R_8$)-M-C($R_7R_8$))—, —(C($R_7$)=C($R_8$))—, —(C($R_7$)=C($R_8$)—C($R_9$)=C($R_{10}$))—, —(C($R_7$)=N)—, or —(C($R_7$)=N—C($R_8$)=N)—; wherein M is oxygen, —N$R_9$—, sulfur, or —C(=O)—; wherein Z is oxygen, sulfur, or —N($R_{11}$)—; wherein $R_5$ and $R_{11}$ are independently selected from hydrogen, alkyl, and aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, and alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —O$R_{12}$, —N(H)($R_{12}$) and —N($R_{12}R_{13}$) wherein $R_{12}$ and $R_{13}$ are independently selected from hydrogen, alkyl and aryl; wherein $R_7$ and $R_8$ may be connected to each other to form a ring structure; and wherein $R_8$ and $R_9$ may be connected to each other to form a ring structure. The acid may be an alcohol, a phenol, or a compound having the formula HX or the formula HTX, wherein X is selected from chloride, bromide, iodide, carboxylate, sulfonate, phosphate, phosphonate, sulfate, and hydroxide (i.e. the acid can be water); and wherein T is selected from imidazole, alkylimidazole, arylimidazole, benzimidazole, alkylbenzimidazole, oxazole, alkyloxazole, benzoxazole, pyrazole, alkylpyrazole, arylpyrazole, pyridine, alkylpyridine, arylpyridine, quinoline, ammonia, and amine.

The invention also includes a system for producing hydrogen ($H_2$). The system includes at least one organic compound, an acid, and a catalyst suitable for facilitating a chemical reaction between the at least one chemical compound and the acid in order to form hydrogen. The chemical compound has the formula

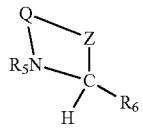

wherein Q is —(C($R_7R_8$))$_n$— where n is from 1 to 10, —(C($R_7R_8$)-M-C($R_7R_8$))—, —(C($R_7$)=C($R_8$))—, —(C($R_7$)=C($R_8$)—C($R_9$)=C($R_{10}$))—, —(C($R_7$)=N)—, or —(C($R_7$)=

N—C($R_8$)=N)—; wherein M is oxygen, —$NR_9$—, sulfur, or —C(=O)—; wherein Z is oxygen, sulfur, or —N($R_{11}$)—; wherein $R_5$ and $R_{11}$ are independently selected from hydrogen, alkyl, and aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, and alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid-$OR_{12}$, —N(H)($R_{12}$) and —N($R_{12}R_{13}$) wherein $R_{12}$ and $R_{13}$ are independently selected from hydrogen, alkyl and aryl; wherein $R_7$ and $R_8$ may be connected to each other to form a ring structure; and wherein $R_8$ and $R_9$ may be connected to each other to form a ring structure. The acid may be an alcohol, a phenol, or a compound having the formula HX or the formula HTX, wherein X is selected from chloride, bromide, iodide, carboxylate, sulfonate, phosphate, phosphonate, sulfate, and hydroxide (i.e. the acid can be water); and wherein T is selected from imidazole, alkylimidazole, arylimidazole, benzimidazole, alkylbenzimidazole, oxazole, alkyloxazole, benzoxazole, pyrazole, alkylpyrazole, arylpyrazole, pyridine, alkylpyridine, arylpyridine, quinoline, ammonia, and amine.

The invention also includes a system for producing hydrogen ($H_2$). The system includes at least one chemical compound having the formula

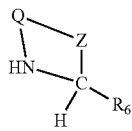

wherein Q is —(C($R_7R_8$))$_n$— where n is from 1 to 10, —(C($R_7R_8$))-M-C($R_7R_8$))—, —(C($R_7$)=C($R_8$))—, —(C($R_7$)=C($R_8$)—C($R_9$)=C($R_{10}$))—, —(C($R_7$)=N)—, —(C($R_7$)=N—C($R_8$)=N—; wherein M is oxygen, —$NR_9$—, sulfur, or —C(=O)—; wherein Z is oxygen, sulfur, or —N($R_{11}$)— wherein $R_{11}$ is hydrogen, alkyl, or aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, and alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —$OR_{12}$, —N(H)($R_{12}$) and —N($R_{12}R_{13}$) wherein $R_{12}$ and $R_{13}$ are independently selected from hydrogen, alkyl and aryl; wherein $R_7$ and $R_8$ may be connected to each other to form a ring structure; and wherein $R_8$ and $R_9$ may be connected to each other to form a ring structure.

The invention also includes a system for producing hydrogen ($H_2$). The system includes at least one chemical compound having the formula

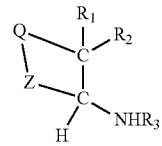

wherein Z is selected from oxygen, sulfur, or —N($R_4$)— where $R_4$ is alkyl or aryl; wherein Q is selected from oxygen, —N($R_5$)—, —(C($R_5R_6$))$_n$— where n is from 1 to 10, —(C($R_5$)=C($R_6$))$_m$— where m is from 1 to 2, and —(C($R_5$)=N)$_p$— where p is from 1 to 2; wherein $R_1$, $R_2$, $R_4$, $R_5$, and $R_6$ are selected independently from alkyl, aryl; and wherein $R_3$ is selected from hydrogen, alkyl, aryl. The system also includes a catalyst suitable for facilitating the dehydrogenation of the chemical compound.

The invention also includes a system for producing hydrogen ($H_2$). The system includes a chemical compound having the formula

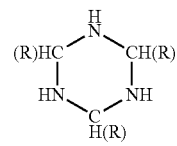

wherein each R is independently selected from hydrogen, alkyl, and aryl; and a catalyst suitable for facilitating the dehydrogenation of the chemical compound.

The invention also includes a system for producing hydrogen ($H_2$) comprising a chemical compound having the formula

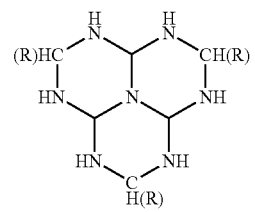

wherein each R is independently selected from hydrogen, alkyl, aryl and a higher fused ring group; and a catalyst suitable for facilitating the dehydrogenation of the chemical compound.

The invention also includes a system for producing hydrogen ($H_2$) comprising a chemical compound having the formula

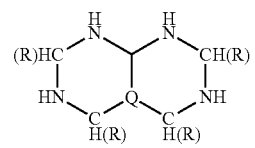

wherein Q is N or (C(R)); wherein each R is independently selected from hydrogen, alkyl, aryl, and a higher fused ring group; and a catalyst suitable for facilitating the dehydrogenation of said chemical compound.

The invention also includes a fuel cell having an anode and a hydrogen-generating fuel source for the anode. The hydrogen-generating fuel source includes at least one chemical compound and a catalyst suitable for dehydrogenating the chemical compound, which has the formula

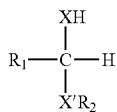

wherein X is oxygen, —N(H)—, or —N($R_3$)—; wherein X' is oxygen, —N(H)— or —N($R_4$)—; wherein $R_1$, $R_2$, $R_3$, and $R_4$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl sulfonic acid, alkenyl phosphoric acid, and alkenyl phosphonic acid; and wherein $R_1$ and $R_3$ can be connected to each other to form a ring structure.

The invention also includes a fuel cell comprising an anode and a hydrogen-generating fuel source for the anode, the hydrogen generating fuel source including at least one chemical compound having the formula

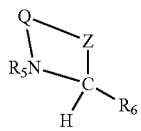

wherein Q is —(C($R_7R_8$))$_n$— where n is from 1 to 10, —(C($R_7R_8$)-M-C($R_7R_8$))—, —(C($R_7$)=C($R_8$))—, —(C($R_7$)=C($R_8$)—C($R_9$)=C($R_{10}$))—, —(C($R_7$)=N—, or —(C($R_7$)=N—C($R_8$)=N)—; wherein M is oxygen, —N$R_9$—, sulfur, or —C(=O)—; wherein Z is oxygen, sulfur, or —N($R_{11}$)—; wherein $R_5$ and $R_{11}$ are independently selected from hydrogen, alkyl, and aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —O$R_{12}$, —N(H)($R_{12}$) and —N($R_{12}R_{13}$) wherein $R_{12}$ and $R_{13}$ are selected from hydrogen, alkyl and aryl; wherein $R_7$ and $R_8$ may be connected to each other to form a ring structure; wherein $R_8$ and $R_9$ may be connected to each other to form a ring structure.

The invention also includes a fuel cell having an anode and a hydrogen-generating fuel source for the anode, the hydrogen generating fuel source including at least one chemical compound having the formula

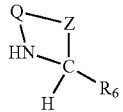

wherein Q is —(C($R_7R_8$))$_n$— where n is from 1 to 10, —(C($R_7R_8$)-M-C($R_7R_8$))—, —(C($R_7$)=C($R_8$))—, —(C($R_7$)=C($R_8$)—C($R_9$)=C($R_{10}$))—, —(C($R_7$)=N—C($R_8$)=N)—; wherein M is oxygen, —N$R_9$—, sulfur, or —C(=O)—; wherein Z is oxygen, sulfur, or —N($R_{11}$)— wherein $R_{11}$ is hydrogen, alkyl, or aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —O$R_{12}$, —N(H)($R_{12}$) and —N($R_{12}R_{13}$) wherein $R_{12}$ and $R_{13}$ are selected from hydrogen, alkyl and aryl; wherein $R_7$ and $R_8$ may be connected to each other to form a ring structure; and wherein $R_8$ and $R_9$ may be connected to each other to form a ring structure.

The invention also includes a fuel cell having an anode and a hydrogen-generating fuel source for the anode, the hydrogen generating fuel source including at least one chemical compound having the formula

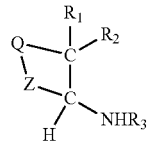

wherein Z is selected from oxygen, sulfur, or —N($R_4$)— where $R_4$ is alkyl or aryl; wherein Q is selected from oxygen, —N($R_5$)—, —(C($R_5R_6$))$_n$— where n is from 1 to 10, —(C($R_5$)=C($R_6$))$_m$— where m is from 1 to 2, and —(C($R_5$)=N)$_p$— where p is from 1 to 2; wherein $R_1$, $R_2$, $R_4$, $R_5$, and $R_6$ are selected independently from alkyl and aryl; and wherein $R_3$ is selected from hydrogen, alkyl, aryl.

The invention also includes a method for storing hydrogen. The method involves exposing at least one chemical compound to hydrogen in the presence of a catalyst that facilitates the hydrogenation of the at least one chemical compound, which has an anion and cationic portion having the formula

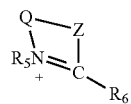

wherein Q is —(C($R_7R_8$))$_n$— where n is from 1 to 10, —(C($R_7R_8$)-M-C($R_7R_8$))—, —(C($R_7$)=C($R_8$))—, —(C($R_7$)=C($R_8$)—C($R_9$)=C($R_{10}$))—, —(C($R_7$)=N)—, or —(C($R_7$)=N—C($R_8$)=N)—; wherein M is oxygen, —N$R_9$—, sulfur, or —C(=O)—; wherein Z is oxygen, sulfur, or —N($R_{11}$)—; wherein $R_5$ and $R_{11}$ are independently selected from hydrogen, alkyl, and aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —$OR_{12}$, —$N(H)(R_{12})$ and —$N(R_{12}R_{13})$ wherein $R_{12}$ and $R_{13}$ are selected from hydrogen, alkyl and aryl; wherein $R_7$ and $R_8$ may be connected to each other to form a ring structure; and wherein $R_8$ and $R_9$ may be connected to each other to form a ring structure.

The invention also includes a method for storing hydrogen, which includes exposing at least one chemical compound to a reducing agent, the chemical compound having an anion and a cationic portion having the formula

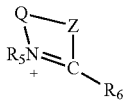

wherein Q is —$(C(R_7R_8))_n$— where n is from 1 to 10, —$(C(R_7R_8)\text{-M-}C(R_7R_8))$—, —$(C(R_7)\!=\!C(R_8))$—, —$(C(R_7)\!=\!C(R_8)\text{—}C(R_9)\!=\!C(R_{10}))$—, —$(C(R_7)\!=\!N)$—, or —$(C(R_7)\!=\!N\text{—}C(R_3)\!=\!N)$—; wherein M is oxygen, —$NR_9$—, sulfur, or —$C(\!=\!O)$—; wherein Z is oxygen, sulfur, or —$N(R_{11})$—; wherein $R_5$ and $R_{11}$ are independently selected from hydrogen, alkyl, and aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, and alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —$OR_{12}$, —$N(H)(R_{12})$ and —$N(R_{12}R_{13})$ wherein $R_{12}$ and $R_{13}$ are selected from hydrogen, alkyl and aryl; wherein $R_7$ and $R_8$ may be connected to each other to form a ring structure; and wherein $R_8$ and $R_9$ may be connected to each other to form a ring structure.

The invention also includes a method for storing hydrogen, and involves exposing at least one chemical compound to hydrogen or to a reducing agent in the presence of a catalyst that facilitates the hydrogenation of the at least one chemical compound, which has the formula

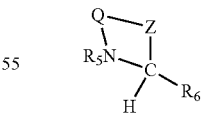

wherein X is oxygen, —$N(H)$—, or —$N(R_3)$—; wherein X' is oxygen, —$N(H)$— or —$N(R_4)$—; wherein $R_1$, $R_2$, $R_3$, and $R_4$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl sulfonic acid, alkenyl phosphoric acid, and alkenyl phosphonic acid; and wherein $R_1$ and $R_3$ can be connected to each other to form a ring structure; and with the proviso that X and X' cannot both be oxygen.

DETAILED DESCRIPTION

The present invention relates to a chemical system useful for chemical hydrogen storage. Using the chemical system of the invention, hydrogen ($H_2$) is evolved without significant input or evolution of heat.

One aspect of the present invention relates to hydrogen evolution from chemical compounds according to equation 6:

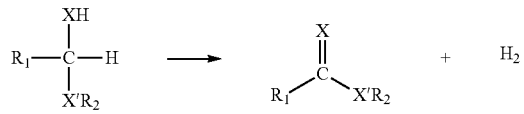

(6)

wherein X is oxygen, —$N(H)$—, or —$N(R_3)$—; wherein X' is oxygen, —$N(H)$— or —$N(R_4)$—; wherein $R_1$, $R_2$, $R_3$, and $R_4$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl sulfonic acid, alkenyl phosphoric acid, and alkenyl phosphonic acid; and wherein $R_1$ and $R_3$ can be connected to each other to form a ring structure; and with the proviso that X and X' cannot both be oxygen.

For equation 6, it is believed that the $\Delta H^0$ varies from about +10 kcal/mole to about −2 kcal/mole, and the $\Delta G^0$ varies from about +5 kcal/mole to about −10 kcal/mole. Thus, the chemical reaction for hydrogen evolution as shown in Equation 6 above is nearly thermoneutral, perhaps even slightly exothermic, based on the currently available thermodynamic data for these materials. Owing to the favorable entropy of hydrogen evolution, the reaction can become exergonic (having a standard free energy change, $\Delta G^0$, of less than zero) and the ambient temperature equilibrium pressure of hydrogen approaches or exceeds the DOE target of 3 atmospheres.

If the chemical compound is stabilized against classical functional group elimination by, for example, the presence of additional atoms that join to form a ring structure, then it is expected that the hydrogen evolution and hydrogenation will be reversible in the presence of a suitably active catalyst that selectively catalyzes the hydrogen evolution reaction and also the reverse reaction (i.e. the hydrogenation reaction). Such reversibility is advantageous because it allows the chemical compound to be regenerated simply by hydrogenation under pressure, and the energy cost of regenerating the chemical compound is likely to be minimal.

Another aspect of the invention is related to a method and chemical system for producing hydrogen. This aspect of the invention involves exposing one or more chemical compounds to a catalyst under conditions suitable for a chemical reaction that forms hydrogen. Chemical compounds that evolve hydrogen according to the present invention include those having the chemical formula

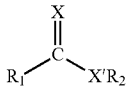

wherein Q is —$(C(R_7R_8))_n$— where n is from 1 to 10, —$(C(R_7R_8)\text{-M-}C(R_7R_8))$—, —$(C(R_7)\!=\!C(R_8))$—, —$(C(R_7)\!=\!C(R_8)\text{—}C(R_9)\!=\!C(R_{10}))$—, —$(C(R_7)\!=\!N)$—, or —$(C(R_7)\!=\!N\text{—}C(R_8)\!=\!N)$—; wherein M is oxygen, —$NR_9$—, sulfur, or —$C(\!=\!O)$—; wherein Z is oxygen, sulfur, or —$N(R_{11})$—; wherein $R_5$ and $R_{11}$ are independently selected from hydrogen, alkyl, and aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, and alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —$OR_{12}$, —$N(H)(R_{12})$ and —$N(R_{12}R_{13})$ wherein $R_{12}$ and $R_{13}$ are independently selected from hydrogen, alkyl and aryl; wherein $R_7$ and $R_8$ may be connected to each other to form a ring structure; wherein $R_8$ and $R_9$ may be connected to each other to form a ring structure; and with the proviso that at least one of $R_5$ or $R_{11}$ is hydrogen. When Q is —$(C(R_7R_8))_n$— where n is greater than one, and when Q is —$(C(R_7R_8)\text{-M-}C(R_7R_8))$—, the invention is meant to include structures where $R_7$ and $R_8$ in one $C(R_7R_8)$ grouping might be the same, but are not necessarily the same, as the $R_7$ and $R_8$ in another $C(R_7R_8)$ grouping. Structures such as the one shown below on the right, for example, where n is two and where $R_7$ and $R_8$ in one grouping are H and methyl, and are ethyl and phenyl in another grouping, are invention structures.

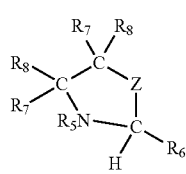 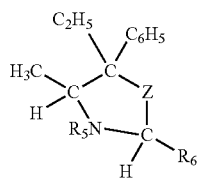

An embodiment system including a chemical compound exemplary of the above formula was used to demonstrate this aspect of the present invention, and is shown in equation 7 below.

While not intending to be bound by any particular explanation, it is believed that the compound shown on the top left of equation 7 tautomerizes to the zwitterionic form shown on the bottom left and that hydrogen evolution from either of these forms produces the species shown on the right.

The hydrogen evolution reaction is a classically "symmetry forbidden" reaction. Therefore, the hydrogen evolution reaction is typically very slow in the absence of a suitable catalyst. Examples of catalysts that may facilitate hydrogen evolution include, for example, rhodium or ruthenium-based hydrogen transfer catalysts, ruthenium-based formic acid decomposition catalysts, nickel/copper/zinc-based reformation/hydrogenation catalysts, and the like. Catalysts useful with the present invention also include various forms of palladium, such as finely divided palladium metal, palladium supported on carbon, palladium supported on alumina, palladium supported on silica, a slurry of palladium in a solvent, a fluidized bed comprising palladium, a packed bed comprising palladium, or palladium carboxylate. For the system shown in equation 7, hydrogen evolution was observed in the presence of a palladium catalyst at a reaction temperature of from room temperature to about 60-70 degrees Celsius (a temperature range of from about 20 degrees Celsius to about 250 degrees Celsius will facilitate the reaction). Interestingly, in the absence of the catalyst, the compound shown top left does not evolve hydrogen after heating at 185 degrees Celsius for 8 days (see P. Brunet and J. D. Wuest "Formal Transfers of Hydride from Carbon-Hydrogen Bonds. Attempted Generation of $H_2$ by Intramolecular Protonolysis of the Activated Carbon-Hydrogen Bonds of Dihydrobenzimidazoles," Can. J. Chem. (1996) vol. 74, p. 689).

The system shown in equation 7 employs an acidic functional group. Other aspects of this invention relate to a method and system that relate to chemical compounds that may, but do not necessarily include acidic functional groups. Compounds of this type could be used with a catalyst and separate (7)

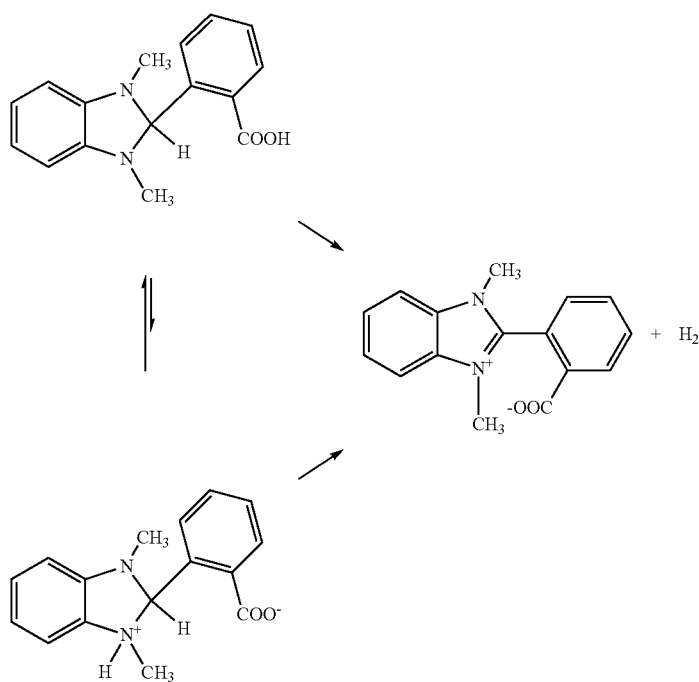

acid. This aspect of the invention relates to evolving hydrogen by exposing at least one chemical compound and an acid to a catalyst under conditions suitable for chemical reaction that forms hydrogen. Chemical compounds of this type have the formula

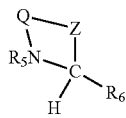

wherein Q is —$(C(R_7R_8))_n$— where n is from 1 to 10, —$(C(R_7R_8)$-M-$C(R_7R_8))$—, —$(C(R_7)$=$C(R_8))$—, —$(C(R_7)$=$C(R_8)$—$C(R_9)$=$C(R_{10}))$—, —$(C(R_7)$=N)—, or —$(C(R_7)$=N—$C(R_8)$=N)—; wherein M is oxygen, —$NR_9$—, sulfur, or —C(=O)—; wherein Z is oxygen, sulfur, or —$N(R_{11})$—; wherein $R_5$ and $R_{11}$ are independently selected from hydrogen, alkyl, and aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, and alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —$OR_{12}$, —$N(H)(R_{12})$ and —$N(R_{12}R_{13})$ wherein $R_{12}$ and $R_{13}$ are independently selected from hydrogen, alkyl and aryl; wherein $R_7$ and $R_8$ may be connected to each other to form a ring structure; and wherein $R_8$ and $R_9$ may be connected to each other to form a ring structure. The acid can be an alcohol (methyl alcohol, ethyl alcohol, trifluoromethyl alcohol, and the like), a phenol (phenol, resorcinol, catechol, naphthol, and the like), or a compound having the formula HX or the formula HTX, wherein X is selected from chloride, bromide, iodide, carboxylate, sulfonate, phosphate, phosphonate, sulfate, and hydroxide (i.e. the acid may be water); and wherein T is selected from imidazole, alkylimidazole, arylimidazole, benzimidazole, alkylbenzimidazole, oxazole, alkyloxazole, benzoxazole, pyrazole, alkylpyrazole, arylpyrazole, pyridine, alkylpyridine, arylpyridine quinoline, ammonia, and amine. Some examples of an acid HX useful with this invention include, but are not limited to, acetic acid, succinic acid, benzoic acid, and acrylic acid. Preferably, the compound and/or the acid HX or HTX is (are) chosen such that the change in the standard free energy of the chemical reaction comprises a standard free energy in the range of from about +5 kilocalories per mole to about −10 kilocalories per mole.

The compound may be dissolved in a solvent chosen to stabilize the at least one organic compound and any cationic reaction products derived therefrom, so that the change in the standard free energy of the chemical reaction comprises a standard free energy in the range of from about +5 kilocalories per mole to about −10 kilocalories per mole. Examples of solvents useful with the present invention include polar organic and inorganic solvents such as, but not limited to, water, acetonitrile, tetrahydrofuran, pyridine, dimethylsulfoxide (DMSO), dimethylformamide (DMF), acetone, methyl ethyl ketone, methanol, ethanol, isopropanol, and the like. Ionic liquid solvents, also know in the art as "molten salts," may also be used as solvents. Ionic liquids useful with this invention have been described, for example, in PCT Patent Application WO 01/93363 to A. McEwen et al. entitled "Non-Flammable Electrolytes"; in Japanese Patent 98168028 to M. Watanabe et al. entitled "Room Temperature Molten Salts and Electrochemical Devices Using the Salts"; in U.S. Pat. No. 6,365,301 to C. Michot et al. entitled "Materials Useful as Electrolytic Solutes," which issued on Apr. 2, 2002; in "Room Temperature Ionic Liquids of Alkylimidazolium Cations and Fluoroanions" by R. Hagiwara and Y. Ito, J. Fluorine Chem. vol. 105, (2000), pp. 221-227; in "Room-Temperature Molten Salts Based on the Quaternary Ammonium Ion" by J. Sun, M. Forsyth, and D. R. MacFarlane, J. Phys. Chem. B, 1998, vol. 102, pages 8858-8864; and in U.S. Pat. No. 5,827,602 to V. R. Koch et al. entitled "Hydrophobic Ionic Liquids," which issued Oct. 27, 1998, all incorporated by reference herein.

Another aspect of this invention relates to a method and system for producing hydrogen that employs compounds having the formula

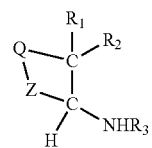

wherein Z is selected from oxygen, sulfur, or —$N(R_4)$— where $R_4$ is alkyl or aryl; wherein Q is selected from oxygen, —$N(R_5)$—, —$(C(R_5R_6))_n$— where n is from 1 to 10, —$(C(R_5)$=$C(R_6))_m$— where m is from 1 to 2, and —$(C(R_5)$=N$)_p$— where p is from 1 to 2 wherein $R_1$, $R_2$, $R_4$, $R_5$, and $R_6$ are selected independently from alkyl, aryl; and wherein $R_3$ is selected from hydrogen, alkyl, aryl. The system also includes a catalyst suitable for facilitating the dehydrogenation of the chemical compound.

Another aspect of the present invention is related to hydrogen storage, and involves exposing at least one chemical compound to a hydrogen in the presence of a catalyst that facilitates the hydrogenation of the at least one chemical compound, which includes anion and cationic portion having the formula

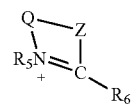

wherein Q is —$(C(R_7R_8))_n$— where n is from 1 to 10, —$(C(R_7R_8)$-M-$C(R_7R_8))$—, —$(C(R_7)$=$C(R_8))$—, —$(C(R_7)$=$C(R_8)$—$C(R_9)$=$C(R_{10}))$—, —$(C(R_7)$=N)—, or —$(C(R_7)$=N— $C(R_8)$=N)—; wherein M is oxygen, —$NR_9$—, sulfur, or —C(=O)—; wherein Z is oxygen, sulfur, or —$N(R_{11})$—; wherein $R_5$ and $R_{11}$ are independently selected from hydrogen, alkyl, and aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —$OR_{12}$, —$N(H)(R_{12})$ and —$N(R_{12}R_{13})$ wherein $R_{12}$ and $R_{13}$ are selected from hydrogen, alkyl and aryl; wherein $R_7$ and $R_8$ may be connected to each other to form a ring structure; and wherein $R_8$ and $R_9$ may be connected to each other to form a ring structure.

The invention also includes a method for storing hydrogen, which includes exposing at least one chemical compound to a reducing agent, the chemical compound having an anion and a cationic portion having the formula

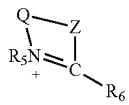

wherein Q is —$(C(R_7R_8))_n$— where n is from 1 to 10, —$(C(R_7R_3)$-M-$C(R_7R_8))$—, —$(C(R_7)$=$C(R_8))$—, —$(C(R_7)$=$C(R_8)$—$C(R_9)$=$C(R_{10}))$—, —$(C(R_7)$=N)—, or —$(C(R_7)$=N—$C(R_8)$=N)—; wherein M is oxygen, —$NR_9$—, sulfur, or —$C(=O)$—; wherein Z is oxygen, sulfur, or —$N(R_{11})$—; wherein $R_5$ and $R_{11}$ are independently selected from hydrogen, alkyl, and aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, and alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —$OR_{12}$, —$N(H)(R_{12})$ and —$N(R_{12}R_{13})$ wherein $R_{12}$ and $R_{13}$ are selected from hydrogen, alkyl and aryl; wherein $R_7$ and $R_8$ may be connected to each other to form a ring structure; and wherein $R_8$ and $R_9$ may be connected to each other to form a ring structure. The reducing agents may one or more of lithium borohydride, sodium borohydride, potassium borohydride, sodium hydride, potassium hydride, magnesium hydride, lithium hydride, calcium hydride, and electron plus proton where the electron can be provided by a metal reducing agent (zinc, for example).

The invention also includes a method for storing hydrogen, and involves exposing at least one chemical compound to hydrogen or to a reducing agent in the presence of a catalyst that facilitates the hydrogenation of the at least one chemical compound, which has the formula

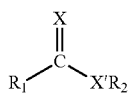

wherein X is oxygen, —N(H)—, or —$N(R_3)$—; wherein X' is oxygen, —N(H)— or —$N(R_4)$—; wherein $R_1$, $R_2$, $R_3$, and $R_4$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl sulfonic acid, alkenyl phosphoric acid, and alkenyl phosphonic acid; and wherein $R_1$ and $R_3$ can be connected to each other to form a ring structure; and with the proviso that X and X' cannot both be oxygen.

Another example of a system for hydrogen evolution and storage is related to chemical compounds known generally as triazacyclohexanes, which are also known in the art as hexahydrotrazines. These materials evolve hydrogen and a product known more generally as a triazine. In this system, three molecules of hydrogen may be produced from one molecule of the triazacyclohexane. The amount of evolvable hydrogen for triazacyclohexane is 6.9 weight percent. The dehydrogenation reaction is slightly endothermic ($\Delta H$=+17 kcal/mole by calculation) and exergonic ($\Delta G$=−9 kcal/mole by calculation). Examples of these types of materials that can be used to produce a hydrogen evolving system of the invention include, for example, a compound having the formula

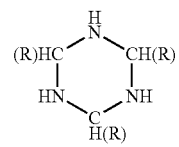

wherein each R is independently selected from hydrogen, alkyl, and aryl; and a compound having the formula

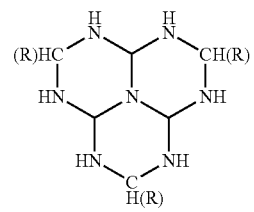

wherein each R is independently selected from hydrogen, alkyl, aryl and a higher fused ring group; and a compound having the formula

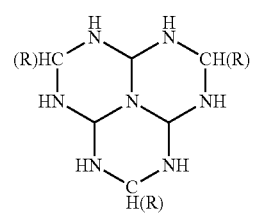

wherein each R is independently selected from hydrogen, alkyl, aryl and a higher fused ring group. For these compounds, a catalyst is included for facilitating the dehydrogenation of the chemical compound.

The method and system of the present invention can be used with a fuel cell to provide power to portable devices such as laptop or handheld computers, cellular phones, global positioning system receivers, CD/MP3 music players, flashlights, and the like, and vehicles. The following details relate to aspects of the invention that relate to fuel cells.

The invention also includes a fuel cell having an anode and a hydrogen-generating fuel source for the anode. The hydrogen-generating fuel source includes at least one chemical compound and a catalyst suitable for dehydrogenating the chemical compound, which has the formula

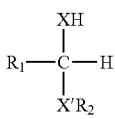

wherein X is oxygen, —N(H)—, or —N($R_3$)—; wherein X' is oxygen, —N(H)— or —N($R_4$)—; wherein $R_1$, $R_2$, $R_3$, and $R_4$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl sulfonic acid, alkenyl phosphoric acid, and alkenyl phosphonic acid; and wherein $R_1$ and $R_3$ can be connected to each other to form a ring structure.

The invention also includes a fuel cell comprising an anode and a hydrogen-generating fuel source for the anode, the hydrogen generating fuel source including at least one chemical compound having the formula

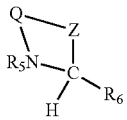

wherein Q is —(C($R_7R_8$))$_n$— where n is from 1 to 10, —(C($R_7R_8$)-M-C($R_7R_8$))—, —(C($R_7$)═C($R_8$))—, —(C($R_7$)═C($R_8$)—C($R_9$)═C($R_{10}$))—, —(C($R_7$)═N)—, or —(C($R_7$)═N—C($R_8$)═N)—; wherein M is oxygen, —N$R_9$—, sulfur, or —C(═O)—; wherein Z is oxygen, sulfur, or —N($R_{11}$)—; wherein $R_5$ and $R_{11}$ are independently selected from hydrogen, alkyl, and aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —O$R_{12}$, —N(H)($R_{12}$) and —N($R_{12}R_{13}$) wherein $R_{12}$ and $R_{13}$ are selected from hydrogen, alkyl and aryl; wherein $R_7$ and $R_8$ may be connected to each other to form a ring structure; wherein $R_8$ and $R_9$ may be connected to each other to form a ring structure; and with the proviso that at least one of $R_5$ or $R_{11}$ is hydrogen.

The invention also includes a fuel cell having an anode and a hydrogen-generating fuel source for the anode, the hydrogen generating fuel source including at least one chemical compound having the formula

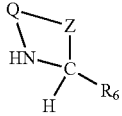

wherein Q is —(C($R_7R_8$))$_n$— where n is from 1 to 10, —(C($R_7R_8$)-M-C($R_7R_8$))—, —(C($R_7$)═C($R_8$))—, —(C($R_7$)═C($R_8$)—C($R_9$)═C($R_{10}$))—, —(C($R_7$)═N)—, —(C($R_7$)═N—C($R_8$)═N)—; wherein M is oxygen, —N$R_9$—, sulfur, or —C(═O)—; wherein Z is oxygen, sulfur, or —N($R_{11}$)— wherein $R_{11}$ is hydrogen, alkyl, or aryl; wherein $R_7$, $R_8$, $R_9$, and $R_{10}$ are independently selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid; wherein $R_6$ is selected from hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —O$R_{12}$, —N(H)($R_{12}$) and —N($R_{12}R_{13}$) wherein $R_{12}$ and $R_{13}$ are selected from hydrogen, alkyl and aryl; wherein $R_7$ and $R_8$ may be connected to each other to form a ring structure; and wherein $R_8$ and $R_9$ may be connected to each other to form a ring structure.

The invention also includes a fuel cell having an anode and a hydrogen-generating fuel source for the anode, the hydrogen generating fuel source including at least one chemical compound having the formula

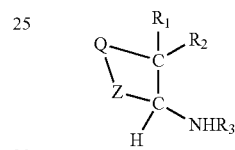

wherein Z is selected from oxygen, sulfur, or —N($R_4$)— where $R_4$ is alkyl or aryl; wherein Q is selected from oxygen, —N($R_5$)—, —(C($R_5R_6$))$_n$— where n is from 1 to 10, —(C($R_5$)═C($R_6$))$_m$— where m is from 1 to 2, and —(C($R_5$)═N)$_p$— where p is from 1 to 2; wherein $R_1$, $R_2$, $R_4$, $R_5$, and $R_6$ are selected independently from alkyl and aryl; and wherein $R_3$ is selected from hydrogen, alkyl, aryl.

With a suitable catalyst, the hydrogen reaction becomes reversible, allowing the organic compounds to function as reversible hydrogen carriers that are capable of carrying hydrogen from one region of a device to another.

The following EXAMPLES illustrate embodiments of the present invention.

Example 1

Catalytic dehydrogenation of

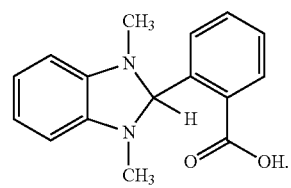

(1)

A solution of compound 1 (9 mg, 0.03 mmol) in CD$_3$CN (0.7 ml) was prepared in a nuclear magnetic resonance (NMR) tube. Palladium acetate (Pd(O$_2$CCH$_3$)$_2$, 1 mg, 0.003 mmol) was added to the tube. Upon mixing, a black precipitate formed and effervescence was observed. The reaction mixture was then heated to a temperature of about 70 degrees Celsius for about 30 minutes, resulting in a 90 percent conversion of (1) to

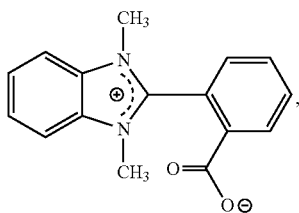

(2)

which was confirmed by ¹H NMR spectroscopy. ¹H NMR (1) (THF-d₈, 25° C., 400 MHz): δ 8.08 (d, 1H, aromatic), δ 7.83 (d, 1H, aromatic), δ 7.53 (t, 1H, aromatic), δ 6.56 (m, 2H, aromatic), δ 6.31 (m, 2H, aromatic), δ 6.00 (s, 1H, RN₂CH), δ 2.50 (s, 6H, CH₃). ¹H NMR (2) (CD₃CN, 25° C., 400 MHz): δ 8.23 (d, 1H, aromatic), δ 7.77 (m, 2H, aromatic), δ 7.72 (t, 1H, aromatic), δ 7.60 (m, 3H, aromatic), δ 7.40 (d, 1H, aromatic), δ 3.52 (s, 6H, CH₃).

Evolution of molecular hydrogen from compound (1) was confirmed by catalytic hydrogenation of trans-stilbene with the hydrogen evolved from compound (1). In an experimental set-up, a flask was charged with compound (1) (50 mg, 0.18 mmol) and Pd(O₂CCH₃)₂ (3 mg, 0.013 mmol) in acetonitrile. A separate flask was charged with trans-stilbene (34 mg, 0.18 mmol) and 10% Pd on carbon (20 mg) in benzene. The headspaces of the two flasks were immediately connected with a transfer tube. After about 12 hours, the contents of both flasks were analyzed using ¹H NMR spectroscopy. Complete conversion of compound (1) to compound (2) was observed for the first flask. Hydrogenation of the trans-stilbene in the second flask was 47% complete, confirming the evolution of hydrogen from compound (1).

Example 2

Compound (1) was converted to compound (2) according to the procedure described in EXAMPLE 1, with the exception that Pearlman's catalyst (Pd(OH)₂/C) was used instead of palladium acetate.

Example 3

Compound (1) was converted to compound (2) according to the procedure described in EXAMPLE 1, with the exception that Pd/C was used instead of palladium acetate.

Example 4

Compound (1) was converted to compound (2) according to the procedure described in EXAMPLE 1, with the exception that PdCl₂(bipyridine) was used instead of palladium acetate.

Example 5

Compound (1) was converted to compound (2) according to the procedure described in EXAMPLE 1, with the exception that K₂PdCl₄ was used instead of palladium acetate.

Example 6

Catalytic dehydrogenation of

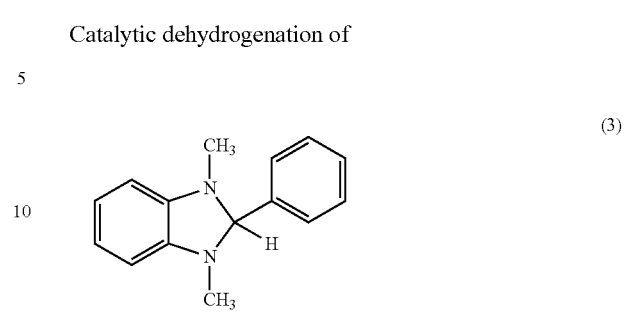

(3)

in the presence of acid. A solution of compound (3) in CD₃CN (0.7 ml) solvent was prepared in an NMR tube. Acetic acid (0.015 ml, 0.26 mmol) was added to the solution and the contents were mixed thoroughly. Palladium acetate (1 mg, 0.003 mmol) was then added to the mixture, after which a black precipitate formed and effervescence was observed. The NMR tube was heated to a temperature of about 70 degrees Celsius for about 30 minutes, resulting in complete conversion of compound 3 to

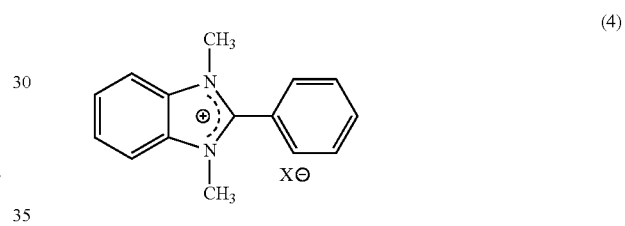

(4)

(X=CH₃COO⁻), which was confirmed by ¹H NMR spectroscopy. ¹H NMR (3) (CD₃CN, 25° C., 400 MHz): δ 7.56-7.45 (m, 5H, aromatic), δ 6.66-6.44 (m, 4H, aromatic), δ 4.84 (s, 1H, N₂RCH), δ 2.50 (s, 6H, NCH₃). ¹H NMR (4) (HX=acetic acid, CD₃CN, 25° C., 300 MHz): δ 8.0-7.6 (m, 9H, aromatic), δ 3.87 (s, 6H, CH₃N), δ 1.80 (s, 3H, CH₃CO₂).

Example 7

Catalytic dehydrogenation of

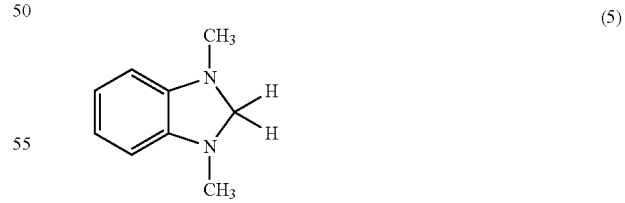

(5)

in the presence of acid and a homogeneous catalyst. A solution of compound 5 (15 mg, 0.10 mmol), acetic acid (60 mg, 1.0 mmol) and CD₃CN (0.70 ml) was prepared in an NMR tube. The solution was mixed, after which RhCl(PPh₃)₃ (0.3 mg, 0.37 μmol, Ph=C₆H₅) was added to the solution. The mixture was heated at a temperature of about 70 degrees Celsius for about one hour, resulting in a 43% conversion of compound (5) to

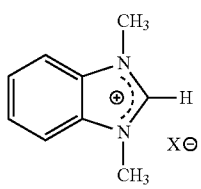

(6)

(X=CH₃COO⁻), which was confirmed by ¹H NMR spectroscopy. Turnover number (TON)=117 at 70° C. in 1 hour. ¹H NMR (5) (CD₃CN, 25° C., 400 MHz): δ 6.65-6.45 (m, 4H, aromatic), δ 4.23 (s, 2H, CH₂), δ 2.68 (s, 6H, NCH₃). ¹H NMR (6) (HX=acetic acid, CD₃CN, 25° C., 400 MHz): δ 10.81 (s, CH₃CO₂), δ 9.07 (s, 1H, NCHN), δ 7.85-7.69 (m, 4H, aromatic), δ 4.05 (s, 6H, NCH₃), δ 1.96 (s, CH₃CO₂).

Example 8

Compound (5) was converted to compound (6) according to the procedure described in EXAMPLE 7 with the exception that CpRuH(PPh₃)₂ (Cp=cyclopentadienyl=C₅H₅) was used instead of RhCl(PPh₃)₃.

Example 9

Compound (5) was converted to compound (6) according to the procedure described in EXAMPLE 7 with the exception that CpRuH(dppe) (dppe=diphenylphosphinoethane) was used instead of RhCl(PPh₃)₃.

Example 10

Compound (5) was converted to compound (6) according to the procedure described in EXAMPLE 7 with the exception that RuCl₂(PPh₃)₃ was used instead of RhCl(PPh₃)₃.

Example 11

Compound (5) was converted to compound (6) according to the procedure described in EXAMPLE 7 with the exception that Pt(CH₃)₂(COD) (COD=cyclooctadiene) was used instead of RhCl(PPh₃)₃.

Example 12

Compound (5) was converted to compound (6) according to the procedure described in EXAMPLE 7 with the exception that Rh(CO)Cl(PPh₃)₂ was used instead of RhCl(PPh₃)₃.

Example 13

Conversion of (5) to (6) in the presence of acid and a heterogeneous catalyst. A solution of compound (5) (15 mg, 0.10 mmol), acetic acid (60 mg, 1.0 mmol) and CD₃CN (0.7 ml) was prepared in an NMR tube. The solution was mixed, and Pd(O₂CCH₃)₂ (1 mg, 0.003 mmol) was added. Effervescence began immediately upon addition of the Pd(O₂CCH₃)₂. Complete conversion of compound (5) to compound (6) (X=CH₃COO⁻) was confirmed by ¹H NMR spectroscopy after 30 minutes at room temperature.

Example 14

Catalytic dehydrogenation of compound (5) in the presence of D₂O and a heterogeneous catalyst. A solution of compound (5) (15 mg, 0.10 mmol) in a 1:1 mixture of D₂O:CD₃OD (0.7 ml) solvent was prepared in an NMR tube. This solution was mixed, Pd(O₂CCH₃)₂ (1 mg, 0.003 mmol) was added, and the resulting mixture was heated to a temperature of about 70 degrees Celsius for about one hour. Effervescence was observed. About a 15 percent conversion of compound (5) to compound (6) (X=OD⁻) after about one hour was confirmed by ¹H NMR spectroscopy.

Example 15

Catalytic dehydrogenation of compound (5) in the presence of D2O, sodium bicarbonate, and a heterogeneous catalyst. A solution of compound (5) (15 mg, 0.10 mmol) and NaHCO3 (0.12 mmol) in a 1:1 mixture of D₂O:CD₃OD (0.7 ml) solvent was prepared in an NMR tube. The solution was mixed, Pd(O₂CCH₃)₂ (1 mg, 0.003 mmol) was added, and the resulting mixture was heated to a temperature of about 70 degrees Celsius for about one hour. Effervescence was observed. ¹H NMR indicated that the conversion from compound (5) to compound (6) (X=bicarbonate or carbonate) was about 15 percent after about one hour.

The foregoing description of the invention has been presented for purposes of illustration and description and is not intended to be exhaustive or to limit the invention to the precise form disclosed, and obviously many modifications and variations are possible in light of the above teaching.

The embodiment(s) were chosen and described in order to best explain the principles of the invention and its'practical application to thereby enable others skilled in the art to best utilize the invention in various embodiments and with various modifications as are suited to the particular use contemplated. It is intended that the scope of the invention be defined by the claims appended hereto.

What is claimed is:

1. A method for producing hydrogen (H₂), comprising exposing a chemical compound to a catalyst under conditions suitable for chemical reaction that forms hydrogen, the chemical compound having the formula

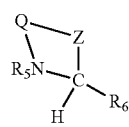

wherein Q is selected from the group consisting of —(C(R₇R₈))ₙ— where n is from 1 to 10, —(C(R₇R₈)-M-C(R₇R₈))—, —(C(R₇)=C(R₈))—, —(C(R₇)=C(R₈)—C(R₉)=C(R₁₀))—, —(C(R₇)=N)—, and —(C(R₇)=N—C(R₈)=N)—;

wherein M is selected from the group consisting of oxygen, —NR₉—, sulfur, and —C(=O)—;

wherein Z is selected from the group consisting of oxygen, sulfur, and —N(R₁₁)—;

wherein R₅ and R₁₁ are independently selected from the group consisting of hydrogen, alkyl, and aryl;

wherein R₇, R₈, R₉, and R₁₀ are independently selected from the group consisting of hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, and alkenyl phosphonic acid;

wherein R₆ is selected from the group consisting of hydrogen, alkyl, aryl, alkenyl, alkyl carboxylic acid, alkyl sulfonic acid, alkyl phosphoric acid, alkyl phosphonic acid, aryl carboxylic acid, aryl sulfonic acid, aryl phosphoric acid, aryl phosphonic acid, alkenyl carboxylic acid, alkenyl phosphoric acid, alkenyl phosphonic acid, —$OR_{12}$, —$N(H)(R_{12})$ and —$N(R_{12}R_{13})$ wherein $R_{12}$ and $R_{13}$ are independently selected from the group consisting of hydrogen, alkyl and aryl;

wherein $R_7$ and $R_8$ may be connected to each other to form a ring structure;

wherein $R_8$ and $R_9$ may be connected to each other to form a ring structure; and with the proviso that at least one of $R_5$ or $R_{11}$ is hydrogen.

2. The method of claim 1, wherein the catalyst comprises palladium.

3. The method of claim 1, wherein the catalyst comprises palladium particles, palladium supported on carbon, palladium supported on alumina, palladium supported on silica, a slurry of palladium in a solvent, a fluidized bed comprising palladium, a packed bed comprising palladium, or palladium carboxylate.

4. The method of claim 1, wherein the catalyst comprises palladium carboxylate dissolved in acetonitrile, tetrahydrofuran, water, or mixtures thereof, or the product resulting from the reaction of palladium carboxylate with acetonitrile, tetrahydrofuran, water, or mixtures thereof.

5. The method of claim 1, wherein Q is —$(C(R_7R_8)\text{-M-C}(R_7R_8))$—, wherein $R_7$ is hydrogen, wherein $R_8$ is hydrogen, wherein M is —$NR_9$—, wherein $R_9$ is hydrogen, wherein Z is —$N(R_{11})$—, and wherein $R_{11}$ is hydrogen.

* * * * *